US00PP22120P2

(12) United States Plant Patent
Takamura

(10) Patent No.: US PP22,120 P2
(45) Date of Patent: Sep. 6, 2011

(54) ***VIOLA* PLANT NAMED 'SUNVIOPINHO'**

(50) Latin Name: *Viola cornuta*
Varietal Denomination: Sunviopinho

(75) Inventor: Naoto Takamura, Yamanashi (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/798,785

(22) Filed: Apr. 10, 2010

(51) Int. Cl.
*A01H 5/00* (2006.01)

(52) U.S. Cl. ..... Plt./323

(58) Field of Classification Search ..... Plt./323
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Viola* plant named 'Sunviopinho', characterized by its semi-upright to outwardly spreading plant habit; vigorous growth habit; freely branching habit; freely flowering habit; and purple violet and white bi-colored flowers.

1 Drawing Sheet

Botanical designation: *Viola cornuta.*
Cultivar denomination: 'SUNVIOPINHO'.

BACKGROUND OF THE INVENTION

The present invention relates to a new and distinct cultivar of *Viola* plant, botanically known as *Viola cornuta* and hereinafter referred to by the name 'Sunviopinho'.

The new *Viola* plant is a product of a planned breeding program conducted by the Inventor in Higashiomi, Shiga, Japan. The objective of the breeding program was to create new semi-upright to outwardly spreading and freely branching *Viola* cultivars with unique and attractive flower coloration.

The new *Viola* plant originated from a cross-pollination made by the Inventor in April, 2004, in Higashiomi, Shiga, Japan, of a proprietary selection of *Viola cornuta* identified as code number VF90-3, not patented, as the female, or seed, parent with a proprietary selection of *Viola cornuta* identified as code number VF193-5, not patented, as the male, or pollen, parent. The new *Viola* plant was discovered and selected by the Inventor as a single flowering plant within the progeny of the stated cross-pollination in a controlled greenhouse environment in Higashiomi, Shiga, Japan in April, 2005.

Asexual reproduction of the new *Viola* plant by vegetative cuttings in a controlled greenhouse environment in Higashiomi, Shiga, Japan since May, 2005, has shown that the unique features of this new *Viola* plant are stable and reproduced true to type in successive generations.

SUMMARY OF THE INVENTION

Plants of the new *Viola* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunviopinho'. These characteristics in combination distinguish 'Sunviopinho' as a new and distinct cultivar of *Viola:*

1. Semi-upright to outwardly spreading plant habit.
2. Vigorous growth habit.
3. Freely branching habit.
4. Freely flowering habit.
5. Purple violet and white bi-colored flowers.

Compared to plants of the female parent selection, plants of the new *Viola* differ primarily in plant size as plants of the female parent selection are smaller than plants of the new *Viola.* In addition, plants of the new *Viola* are more freely branching than plants of the female parent selection.

Compared to plants of the male parent selection, plants of the new *Viola* differ primarily in flower color as plants of the male parent selection have light purple and light yellow-colored flowers. In addition, plants of the new *Viola* are larger than plants of the male parent selection.

Plants of the new *Viola* can also be compared to plants of the *Viola cornuta* 'Sunviolabu', disclosed in U.S. Plant Pat. No. 20,264. In side-by-side comparisons conducted in Higashiomi, Shiga, Japan, plants of the new *Viola* and 'Sunviolabu' differed in the following characteristics:

1. Plants of the new *Viola* had shorter lateral branches than plants of 'Sunviolabu'.
2. Plants of the new *Viola* had larger leaves than plants of 'Sunviolabu'.
3. Plants of the new *Viola* and 'Sunviolabu' differed in flower color as plants of 'Sunviolabu' had light violet-colored flowers.
4. Plants of the new *Viola* had shorter flower spurs than plants of 'Sunviolabu'.
5. Plants of the new *Viola* had shorter peduncles than plants of 'Sunviolabu'.

BRIEF DESCRIPTION OF THE PHOTOGRAPHS

The accompanying colored photographs illustrate the overall appearance of the new *Viola* plant, showing the colors as true as it is reasonably possible to obtain in colored reproductions of this type. Colors in the photographs may differ slightly from the color values cited in the detailed botanical description which accurately describe the colors of the new *Viola* plant.

The photograph at the top of the sheet comprises a top perspective view of a typical flowering plant of 'Sunviopinho' grown in a container.

The photograph at the bottom of the sheet is a close-up view of a typical flowering plant of 'Sunviopinho'.

DETAILED BOTANICAL DESCRIPTION

The aforementioned photographs and following observations, measurements and values describe plants grown in 15-cm containers in Higashiomi, Shiga, Japan, under commercial practice during the winter and spring in a polyethylene-covered greenhouse with day temperatures ranging from 10° C. to 23° C. and night temperatures ranging from −2° C. to 6° C. Plants were five and four months old when the description and photographs, respectively, were taken. In the following description, color references are made to The Royal Horticultural Society Colour Chart, 2001 Edition, except where general terms of ordinary dictionary significance are used.

Botanical classification: *Viola cornuta* 'Sunviopinho'.

Parentage:

*Female, or seed, parent.*—Proprietary selection of *Viola cornuta* identified as code number VF90-3, not patented.

*Male, or pollen, parent.*—Proprietary selection of *Viola cornuta* identified as code number VF193-5, not patented.

Propagation:

*Type.*—By vegetative cuttings.

*Time to initiate roots, summer.*—About two weeks at 20° C. to 25° C.

*Time to initiate roots, winter.*—About two weeks at 15° C. to 20° C.

*Time to produce a rooted young plant roots, summer.*—About four weeks at 20° C. to 25° C.

*Time to produce a rooted young plant roots, winter.*—About four weeks at 15° C. to 20° C.

*Root description.*—Fine, fibrous; white in color.

*Rooting habit.*—Freely branching.

Plant description:

*Plant form/habit.*—Semi-upright and outwardly spreading plant habit; vigorous growth habit; freely branching habit, pinching enhances branching.

*Plant height.*—About 11.6 cm.

*Plant width (spread).*—About 33.4 cm.

*Lateral branches.*—Length: About 13.4 cm. Diameter: About 2.6 mm. Internode length: About 1.4 cm. Aspect: Decumbent. Texture: Smooth, glabrous. Color: Close to 144A.

Foliage description:

*Arrangement.*—Alternate, simple.

*Length.*—About 3.1 cm.

*Width.*—About 2.2 cm.

*Shape.*—Ovate to elliptical.

*Apex.*—Rounded to obtuse.

*Base.*—Truncate.

*Margin.*—Crenate, shallow.

*Texture, upper and lower surfaces.*—Smooth, glabrous.

*Venation pattern.*—Pinnate; reticulate.

*Color.*—Developing and fully expanded leaves, upper surface: Close to 146B; venation, close to 144B. Developing and fully expanded leaves, lower surface: Close to 146C; venation, close to 144B.

*Petiole.*—Length: About 3.2 cm. Diameter: About 1 mm. Texture, upper and lower surfaces: Smooth, glabrous. Color, upper and lower surfaces: Close to 144B.

*Stipule.*—Length: About 2.7 cm. Diameter: About 1.1 cm. Shape: Pinnately-parted. Apex: Obtuse. Base: Cuneate. Texture, upper and lower surfaces: Smooth, glabrous. Color, upper surface: Close to 146B. Color, lower surface: Close to 146C.

Flower description:

*Flower type/habit.*—Single flowers borne in upper leaf axils; flowers face obliquely outward; freely flowering habit with about 32 flowers per plant.

*Fragrance.*—Slightly scented; pleasant.

*Natural flowering season.*—Plants begin flowering about eight to ten weeks after planting; continuously flowering from early November to May in Japan.

*Postproduction longevity.*—Flowers last about five to seven days on the plant; flowers not persistent.

*Flower buds.*—Height: About 1.5 cm. Diameter: About 4 mm. Shape: Lenticular. Color: Close to N81A.

*Flower diameter.*—About 4.2 cm by 3.2 cm.

*Flower depth.*—About 1.6 cm.

*Eye diameter.*—About 4.2 mm by 2.9 mm.

*Petals.*—Quantity per flower: Five in a single whorl; two upper petals, two lateral petals and one lower petal, spurred. Upper petals: Length: About 2.1 cm. Diameter: About 2.1 cm. Shape: Obovate with rounded to truncate apex and attenuate base; margin, entire and slightly undulate. Texture, upper and lower surfaces: Smooth, glabrous. Color: Developing and fully expanded petals, upper surface: Close to N81A to N81D. Developing and fully expanded petals, lower surface: Close to N81A to N81D. Lateral petals: Length: About 1.6 cm. Diameter: About 1.4 cm. Shape: Elliptic with rounded apex and attenuate base; margin, entire and slightly undulate. Texture, upper and lower surfaces: Smooth, glabrous. Color: Developing and fully expanded petals, upper surface: Close to 155C; central apical blotch, close to N82B; stripes at base, close to 86A. Developing and fully expanded petals, lower surface: Close to 155C; central apical blotch, close to N82B. Lower petal: Length: About 1.6 cm. Diameter: About 2.2 cm. Shape: Reniform with cordate apex and attenuate base; margin, entire and slightly undulate. Texture, upper and lower surfaces: Smooth, glabrous. Color: Developing and fully expanded petals, upper surface: Close to 155C; central apical blotch, close to N82B; stripes at base, close to N92A. Developing and fully expanded petals, lower surface: Close to 155C; central apical blotch, close to N82B. Eye color: Close to 17A. Spur length: About 3.8 mm. Spur diameter: About 0.9 mm. Spur color: Close to 90B.

*Sepals.*—Quantity per flower: Typically five in a single whorl. Length: About 1.7 cm. Width: About 3.8 mm. Shape: Lanceolate. Apex: Acute. Base: Truncate. Margin: Entire. Texture, upper and lower surfaces: Smooth, glabrous. Color, upper and lower surfaces: Close to 144A.

*Peduncles.*—Length: About 6.5 cm. Diameter: About 1.1 mm. Texture: Smooth, glabrous. Color: Close to 144A.

*Reproductive organs.*—Stamens: Quantity per flower: Typically five. Anther shape: Ellipsoidal. Anther size:

About 1.9 mm by 1.2 mm. Anther color: Close to 166B; towards the apex, close to 159C. Pollen amount: Scarce. Pollen color: Yellow. Pistils: Quantity per flower: One. Pistil length: About 4.6 mm. Stigma shape: Ellipsoidal. Stigma color: Close to 151B. Ovary color: Close to 145B.

*Seed/fruit.*—Seed and fruit development have not been observed.

Disease/pest resistance: Plants of the new *Viola* have not been noted to be resistant to pathogens and pests common to *Viola*.

Garden performance: Plants of the new *Viola* have been observed to have good garden performance and to tolerate rain, wind and temperatures from about −7° C. to about 25° C.

It is claimed:

1. A new and distinct *Viola* plant named 'Sunviopinho' as illustrated and described.

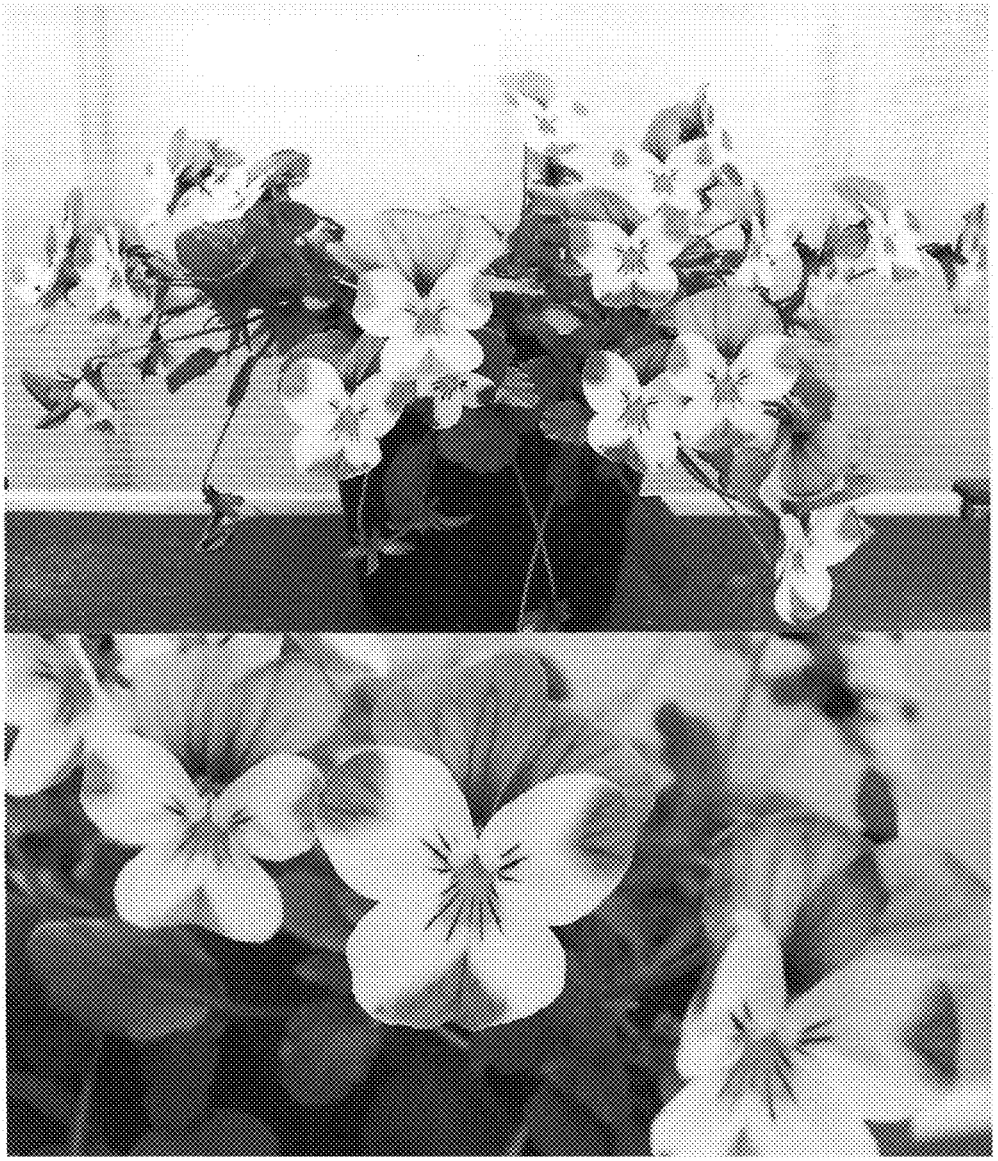

* * * * *